(12) United States Patent
Rockrohr

(10) Patent No.: US 10,420,620 B2
(45) Date of Patent: Sep. 24, 2019

(54) ROBOTIC SURGICAL SYSTEMS, INSTRUMENT DRIVE UNITS, AND DRIVE ASSEMBLIES

(71) Applicant: Covidien LP, Mansfield, MA (US)

(72) Inventor: Brian Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 238 days.

(21) Appl. No.: 15/549,005

(22) PCT Filed: Mar. 9, 2016

(86) PCT No.: PCT/US2016/021432
§ 371 (c)(1),
(2) Date: Aug. 4, 2017

(87) PCT Pub. No.: WO2016/144998
PCT Pub. Date: Sep. 15, 2016

(65) Prior Publication Data
US 2018/0028271 A1    Feb. 1, 2018

Related U.S. Application Data

(60) Provisional application No. 62/130,669, filed on Mar. 10, 2015.

(51) Int. Cl.
*A61B 34/00* (2016.01)
*A61B 34/30* (2016.01)
(Continued)

(52) U.S. Cl.
CPC ............. *A61B 34/71* (2016.02); *A61B 17/29* (2013.01); *A61B 34/30* (2016.02); *A61B 34/35* (2016.02);
(Continued)

(58) Field of Classification Search
CPC ... A61B 34/71; A61B 34/35; A61B 2034/715; A61B 17/29; A61B 2017/00477;
(Continued)

(56) References Cited

U.S. PATENT DOCUMENTS

| 5,779,130 | A | 7/1998 | Alesi et al. |
| 8,337,515 | B2 | 12/2012 | Viola et al. |

(Continued)

FOREIGN PATENT DOCUMENTS

| EP | 0705571 | 4/1996 |
| EP | 0705571 A1 | 4/1996 |
| WO | 2015-088647 A1 | 6/2015 |

OTHER PUBLICATIONS

International Search Report for (PCT/US2016/021432) date of completion is May 18, 2016 (5 pages).

(Continued)

*Primary Examiner* — Jeremy R Severson

(57) ABSTRACT

A drive assembly of an instrument drive unit, is provided. The drive assembly includes a drive screw, a drive nut, a follower, a biasing element, and a drive element. The drive nut is threadedly engaged with a threaded portion of the drive screw such that rotation of the drive screw results in longitudinal movement of the drive nut. The follower is longitudinally slidable with respect to the drive screw. The biasing element is disposed in mechanical cooperation with the drive nut and the follower. The drive element is disposed in mechanical cooperation with the follower. Longitudinal translation of the drive element is configured to drive a function of the surgical instrument.

20 Claims, 8 Drawing Sheets

(51) Int. Cl.
  *A61B 34/35* (2016.01)
  *F16C 1/12* (2006.01)
  *F16H 25/20* (2006.01)
  *A61B 17/29* (2006.01)
  *A61B 17/00* (2006.01)

(52) U.S. Cl.
  CPC ........... *F16C 1/12* (2013.01); *F16H 25/2015* (2013.01); *A61B 17/00234* (2013.01); *A61B 2017/00199* (2013.01); *A61B 2017/00398* (2013.01); *A61B 2017/00477* (2013.01); *A61B 2034/305* (2016.02); *A61B 2034/715* (2016.02); *F16H 2025/204* (2013.01); *F16H 2025/2031* (2013.01); *F16H 2025/2075* (2013.01)

(58) Field of Classification Search
  CPC .............. A61B 34/30; A61B 17/00234; A61B 2017/00199; A61B 2017/00398; F16C 1/12; F16H 25/2015; F16H 2025/2031; F16H 2025/204; F16H 2034/305; F16H 2025/2075
  See application file for complete search history.

(56) References Cited

U.S. PATENT DOCUMENTS

| | | | |
|---|---|---|---|
| 8,828,023 | B2 | 9/2014 | Neff et al. |
| 9,506,542 | B2* | 11/2016 | Wu .................. F16H 25/20 |
| 2008/0308601 | A1 | 12/2008 | Timm et al. |
| 2013/0325034 | A1 | 12/2013 | Schena et al. |
| 2014/0005653 | A1 | 1/2014 | Shelton, IV et al. |
| 2014/0005695 | A1 | 1/2014 | Shelton, IV |
| 2014/0303434 | A1 | 10/2014 | Farritor et al. |
| 2018/0360458 | A1* | 12/2018 | Tapia Espriu ......... A61B 17/10 |
| 2019/0008600 | A1* | 1/2019 | Pedros ................... A61B 17/00 |

OTHER PUBLICATIONS

Extended European Search Report corresponding to counterpart Patent Application EP 16762367.7 dated Dec. 14, 2018.

* cited by examiner

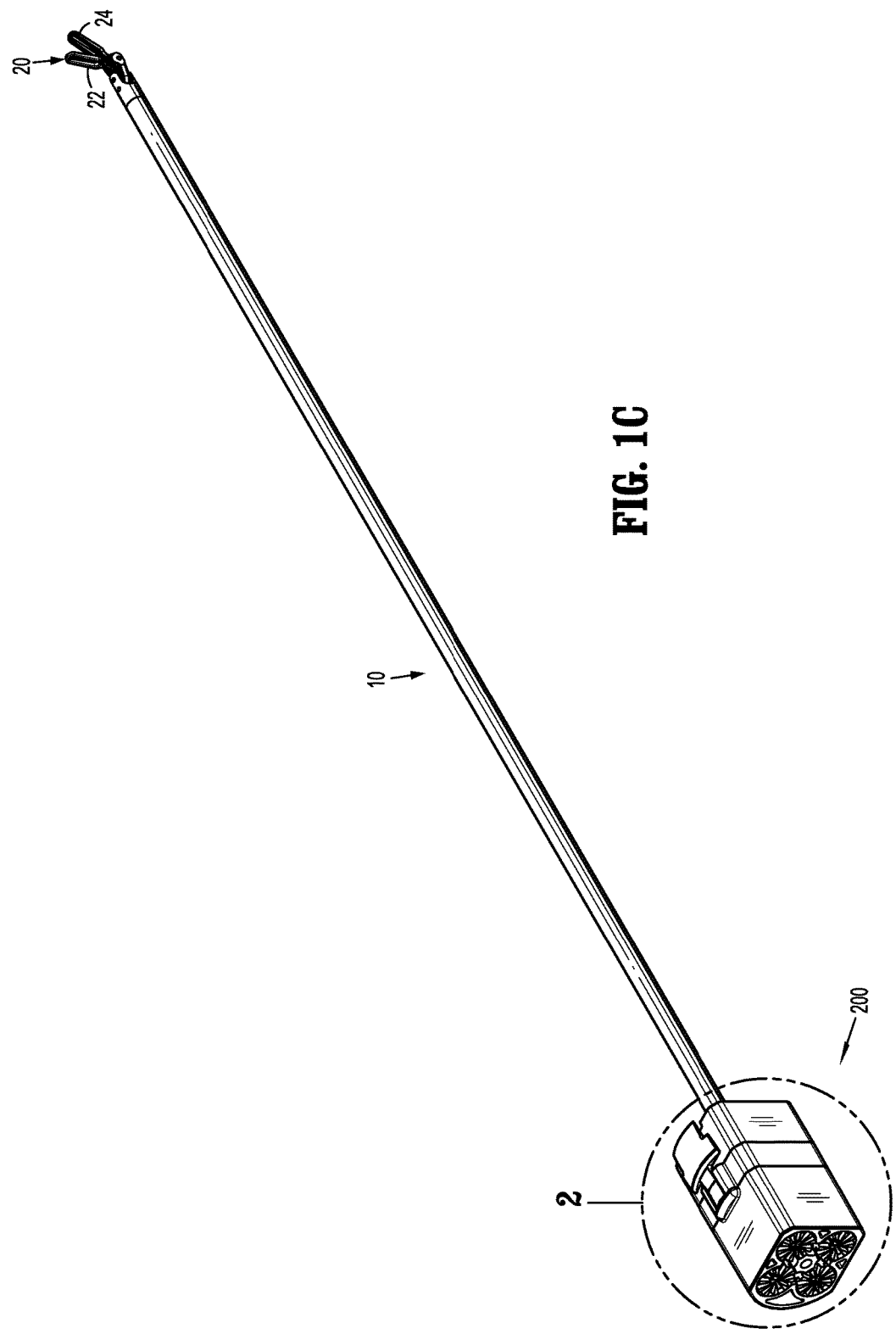

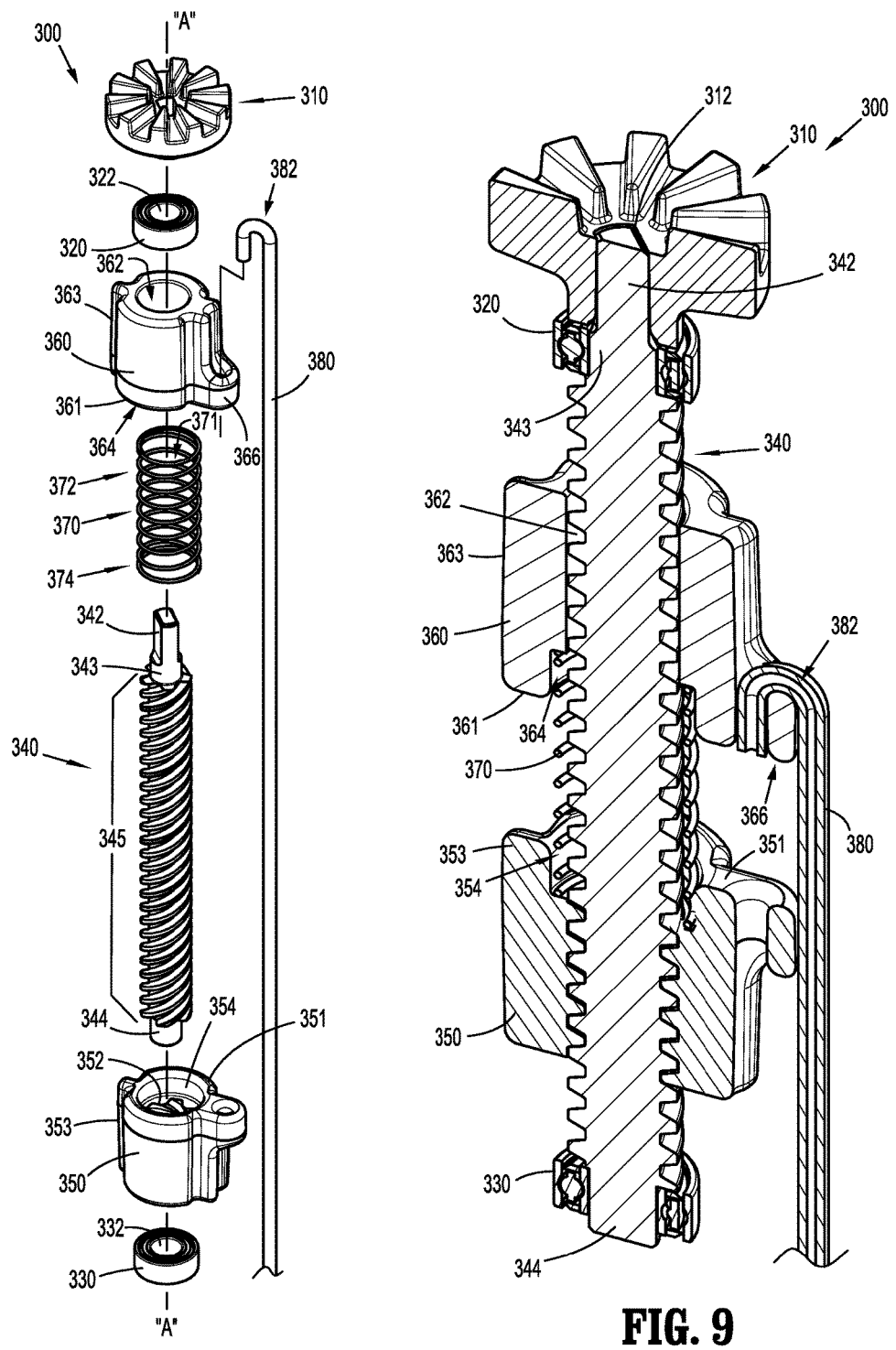

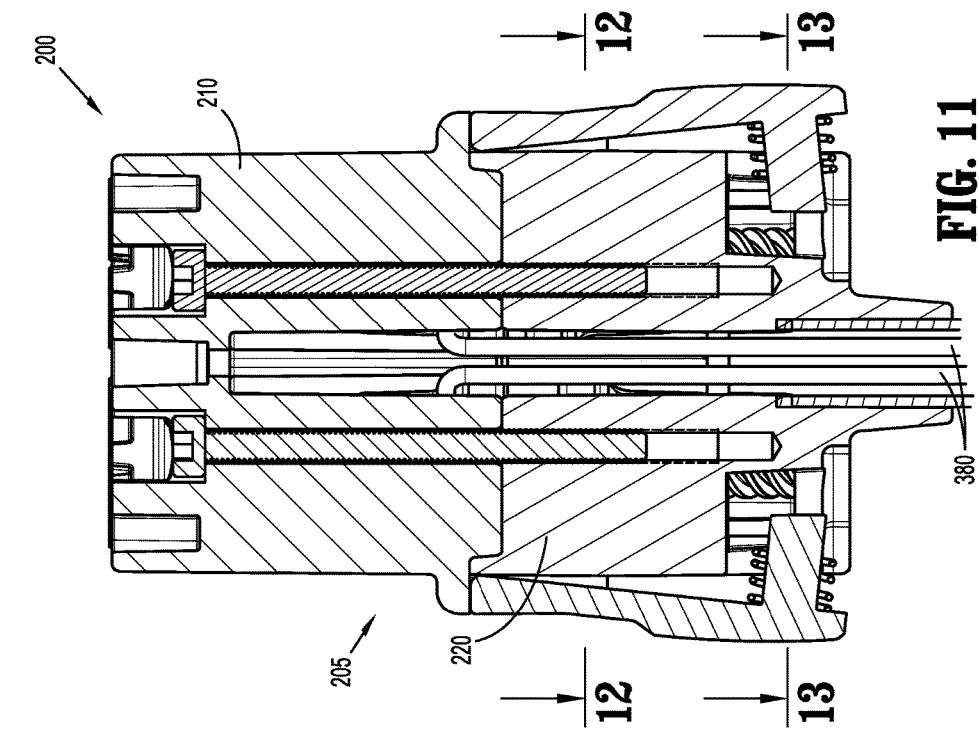
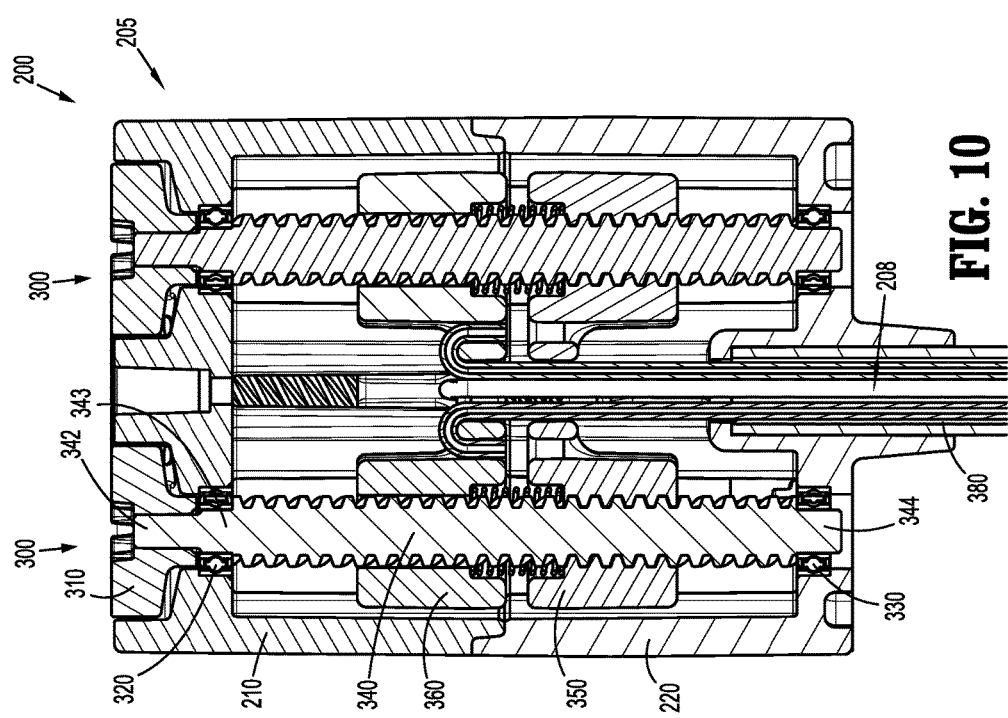
FIG. 10
FIG. 11

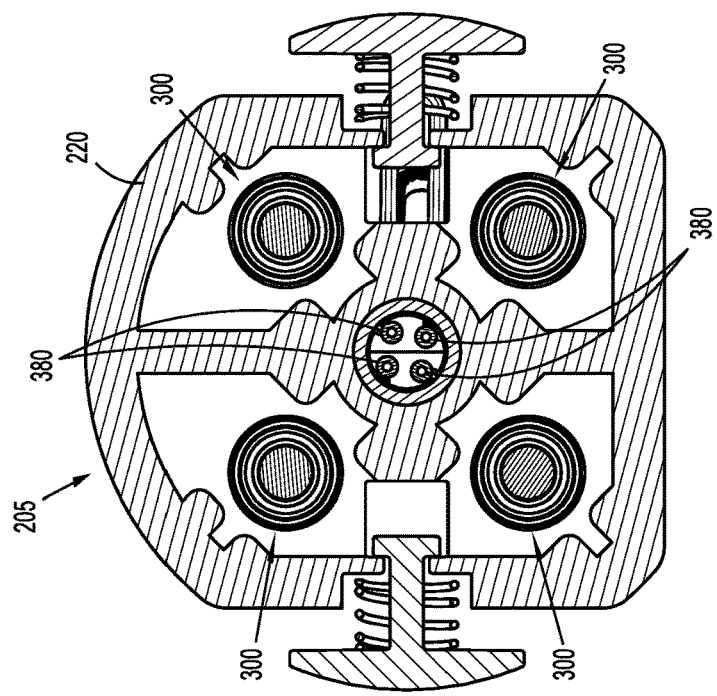
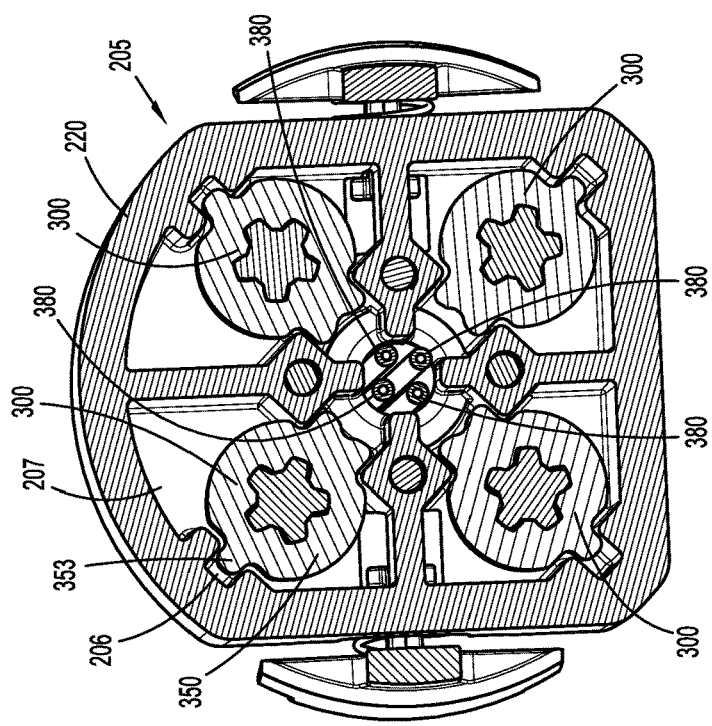

ROBOTIC SURGICAL SYSTEMS, INSTRUMENT DRIVE UNITS, AND DRIVE ASSEMBLIES

CROSS-REFERENCE TO RELATED APPLICATIONS

This application is a U.S. National Stage Application filed under 35 U.S.C. § 371(a) of International Patent Application Serial No. PCT/US2016/021432, filed Mar. 9, 2016, which claims the benefit of and priority to U.S. Provisional Patent Application Ser. No. 62/130,669, filed Mar. 10, 2015, the entire disclosure of which are incorporated by reference herein.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

Cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

In some instances, the wrist assembly provides three degrees of freedom for movement of the end effector through the use of cables or cable pairs, one for each degree of freedom. For example, for grasping or cutting end effectors, the wrist assembly provides the three degrees of freedom by allowing changes to a pitch, a yaw, and an opening and closing of the end effector.

Prior to or during use of the robotic system, surgical instruments are selected and connected to instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, cables for actuating functions of the surgical instrument can lose their tension force and become slack upon manipulation of the jaw members of the surgical instrument, for example.

Accordingly, there is a need for instrument drive units that maintain tension in these cables both in a passive state and in an active state.

SUMMARY

The present disclosure relates to a drive assembly of an instrument drive unit for use with a surgical instrument. The drive assembly includes a drive screw, a drive nut, a follower, a biasing element, and a drive element. The drive screw defines a longitudinal axis and includes a threaded portion. The drive nut is threadedly engaged with the threaded portion of the drive screw such that rotation of the drive screw results in longitudinal movement of the drive nut. The follower is longitudinally slidable with respect to the drive screw. The biasing element is disposed in mechanical cooperation with the drive nut and the follower. The drive element is disposed in mechanical cooperation with the follower. Longitudinal translation of the drive element is configured to drive a function of the surgical instrument.

In disclosed embodiments, the follower is disposed proximally of the drive nut, and the follower is biased proximally.

It is also disclosed that the drive element is secured to the follower, and that the drive element is longitudinally translatable with respect to the drive nut.

It is further disclosed that each of the drive nut and the follower includes a retention pocket configured to house a portion of the biasing element.

In disclosed embodiments, the biasing element is a compression spring.

Additionally, it is disclosed that the follower is disposed proximally of the drive nut, and the drive element extends distally from the follower.

It is also disclosed that the follower is non-threadedly engaged with the drive screw.

It is further disclosed that the drive member includes a flexible cable.

In disclosed embodiments, the drive nut defines an aperture, the follower defines an aperture, and the drive screw extends through the aperture of the drive nut and through the aperture of the follower. It is also disclosed that the biasing element is disposed about the drive screw.

The present disclosure also relates to an instrument drive unit for use with a surgical instrument. The instrument drive unit includes a plurality of drive assemblies. Each drive assembly includes a drive screw, a drive nut, a biasing element, and a flexible drive element. The drive screw defines a longitudinal axis, and includes a threaded portion. The drive nut is threadedly engaged with the threaded portion of the drive screw such that rotation of the drive screw results in longitudinal movement of the drive nut. The biasing element is disposed in mechanical cooperation with the drive nut. The flexible drive element is disposed in mechanical cooperation with the biasing element. Longitudinal translation of the flexible drive element is configured to drive a function of jaw members of the surgical instrument.

In disclosed embodiments, each drive assembly further includes a follower longitudinally slidable with respect to the drive screw.

It is further disclosed that the biasing element is configured to maintain the flexible drive element in a tensile state during application of a mechanical force to the jaw members of the surgical instrument.

Additionally, it is disclosed that the biasing element is a compression spring.

It is also disclosed that the drive nut defines an aperture, and that the drive screw extends through the aperture of the drive nut. It is further disclosed that the biasing element is disposed about the drive screw.

In disclosed embodiments, the plurality of drive assemblies includes four drive assemblies.

It is further disclosed that the instrument drive unit includes a housing, and that each drive assembly of the plurality of drive assemblies is housed at least partially within the housing. The flexible drive element of each drive assembly extends through a central bore of the housing.

In disclosed embodiments, the drive nut and/or the follower include a rail that is configured to slidingly engage a channel of the housing.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 1C is a perspective view of an instrument drive unit in accordance with embodiments of the present disclosure;

FIG. 8 is an exploded view of the drive assembly of FIGS. 5-7;

FIG. 9 is a perspective, cross-sectional view of the drive assembly of FIGS. 5-8, as taken along line 9-9 of FIG. 5;

FIG. 10 is a cross-sectional view of the instrument drive unit of the present disclosure taken along line 10-10 of FIG. 2;

FIG. 11 is a cross-sectional view of the instrument drive unit of the present disclosure taken along line 11-11 of FIG. 2;

FIG. 12 is a transverse cross-sectional view of the instrument drive unit of the present disclosure taken along line 12-12 of FIG. 11; and FIG. 13 is a transverse cross-sectional view of the instrument drive unit of the present disclosure taken along line 13-13 of FIG. 11.

DETAILED DESCRIPTION

Figure 1B:
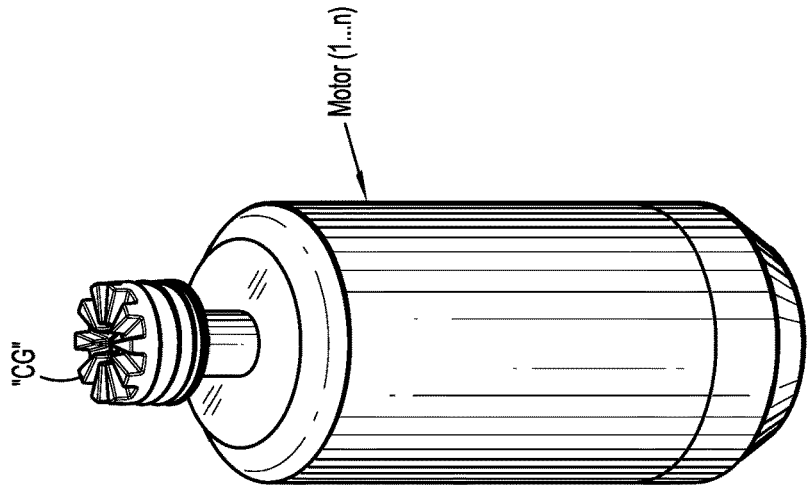
FIG. 1B is a schematic, perspective view of a motor of a control device of the medical work station of FIG. 1A.

Embodiments of the presently disclosed instrument drive units are described in detail with reference to the drawings, in which like reference numerals designate identical or corresponding elements in each of the several views. As used herein the term "distal" refers to that portion of the instrument drive unit that is farther from the user, while the term "proximal" refers to that portion of the instrument drive unit that is closer to the user.

Figure 1A:
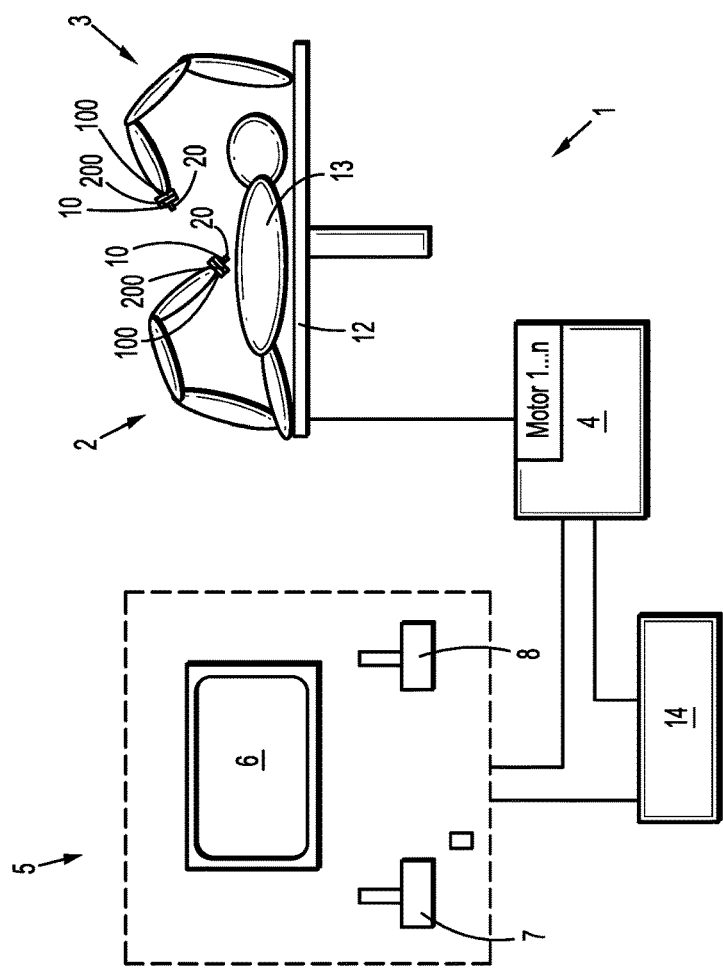
FIG. 1A is a schematic illustration of a medical work station and operating console in accordance with the present disclosure.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument control unit 100, to which may be attached, for example, a surgical instrument 10 having an instrument drive unit 200, and supporting an end effector 20 having jaw members 22 and 24, in accordance with the embodiments of instrument drive units 200 disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units 100, and thus the surgical instruments 10 execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of surgical instrument 10. Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to with control device 4, in which are stored for example pre-operative data from patient 13 and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (e.g., "M1"-"M6"). Motors may be part of instrument control unit 100 and/or disposed externally of instrument control unit 100. Motors "M" (e.g., motors "M" being located externally of instrument control unit 100) may be configured to rotate a crown gear "CG" (FIG. 1B), or the like, that is keyed to or non-rotatably supported on a rotatable shaft of at least some of motors "M." In use, as motors "M" are driven, the rotation of crown gear(s) "CG" effects operation and/or movement of instrument drive unit 200 of surgical instrument 10, as discussed below. It is further envisioned that at least one motor "M" receives signals wirelessly (e.g., from control device 4). It is contemplated that control device 4 coordinates the activation of the various motors (Motor 1 . . . n) to coordinate an operation and/or movement of surgical instrument 10. It is envisioned that each motor corresponds to a separate degree of freedom of surgical instrument 10 engaged with instrument control unit 100. It is further envisioned that more than one motor, including every motor (Motor 1 . . . n), is used for each degree of freedom. Reference may be made to commonly owned International Patent Application No. PCT/US14/61329, filed on Oct. 20, 2014 entitled "Wrist and Jaw Assemblies for Robotic Surgical Systems," the entire content of which is incorporated herein by reference, for a detailed discussion of illustrative examples of the construction and operation of end effectors 20 for use with instrument control unit 100.

Turning now to FIGS. 1C-13, instrument drive unit 200 is shown having surgical instrument 10 extending distally therefrom, and which is configured to engage instrument control unit 100, as described above. Instrument drive unit 200 is configured to transfer rotational movement supplied by instrument control unit 100 (e.g., via motors "M") into longitudinal movement of drive members 380 to effect various functions of end effector 20.

Figure 2:
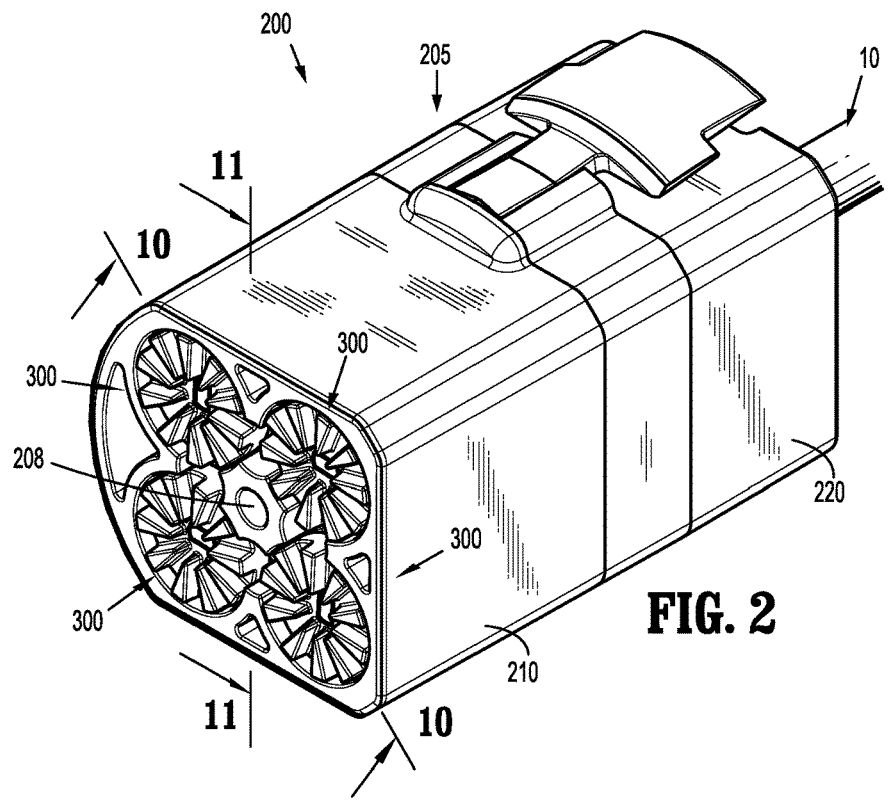
FIG. 2 is enlarged view of the area of detail indicated in FIG. 1C.
Figure 3:
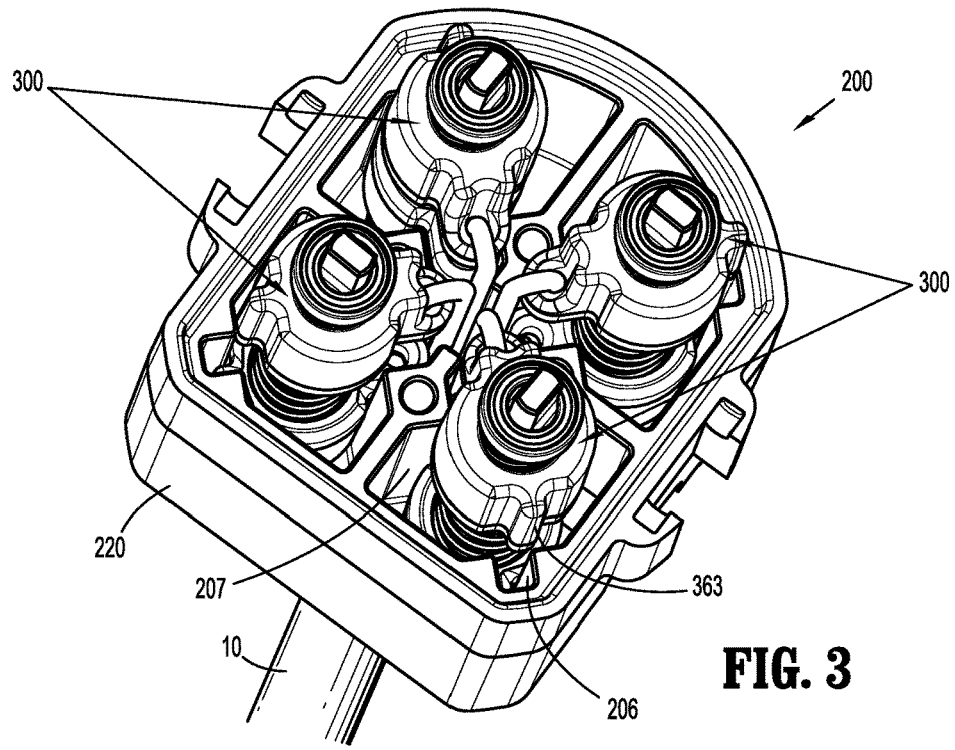
FIG. 3 is a distally-facing perspective view of a portion of the instrument drive unit of FIGS. 1C and 2 with various parts removed therefrom.
Figure 4:
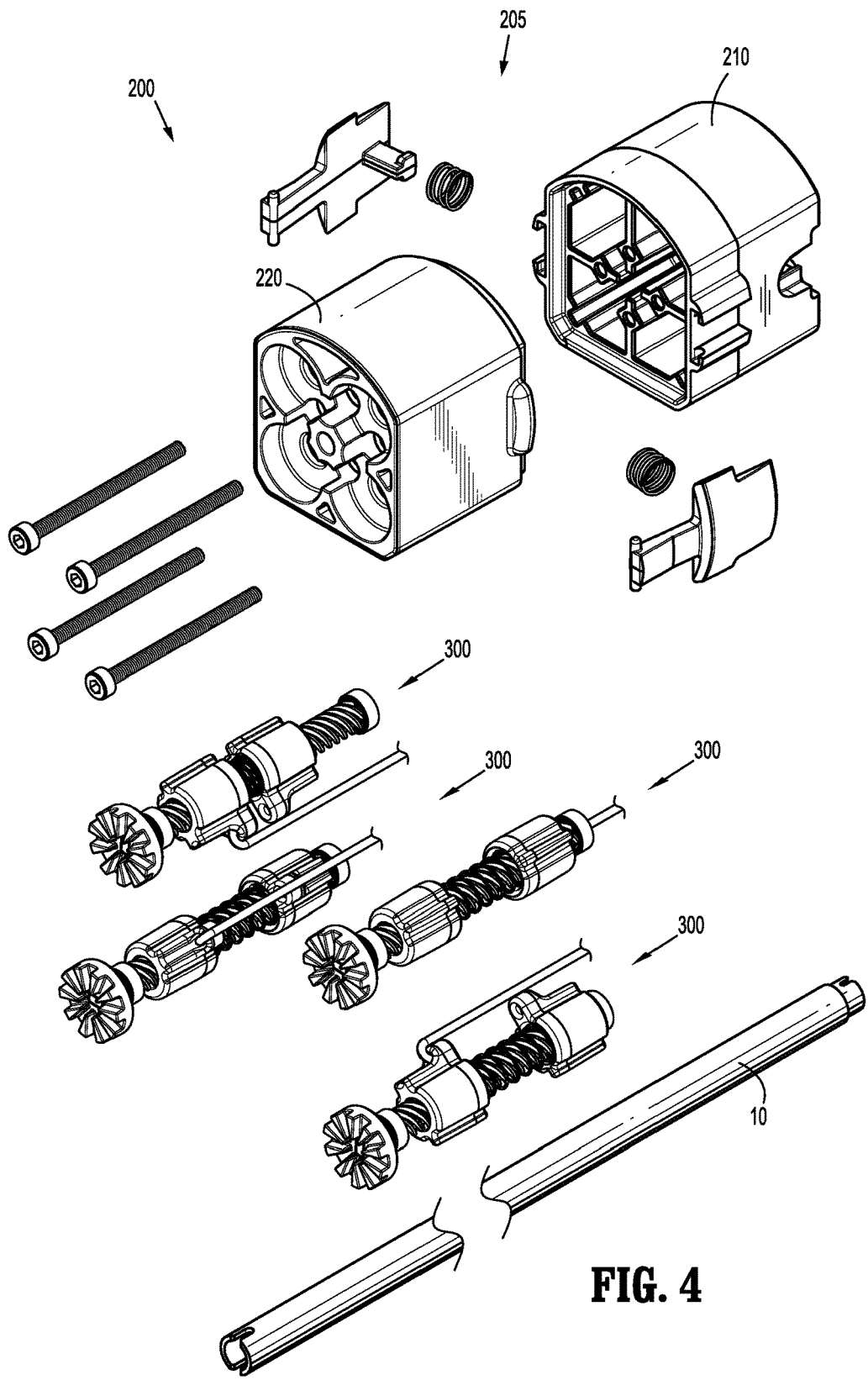
FIG. 4 is an exploded view of the instrument drive unit of FIGS. 1C-3.

With reference to FIGS. 2-4, instrument drive unit 200 includes a housing assembly 205 which includes a proximal housing 210 and a distal housing 220. Proximal housing 210 and distal housing 220 are releasably coupled to each other, which may facilitate assembly of instrument drive unit 200, and which may facilitate access, repair, and/or replacement of parts housed at least partially therein. Housing assembly 205 defines at least one bore 207 for housing drive assemblies 300. It is envisioned that housing assembly 205 includes four separate bores 207, where each bore 207 is at least partially separated from each other and where each bore 207 is configured to house a single drive assembly 300. Additionally, as discussed below, bore 207 includes longitudinally-extending channels 206 (e.g., four channels 206) therein. Each channel 206 is configured to slidingly accept a rail 353 of drive nut 350 and a rail 363 of follower 360. It is further envisioned that each bore 207 includes two separate channels 206, where one channel 206 is configured to slidingly accept rail 353 of drive nut 350 and where the other channel 206 is configured to slidingly accept rail 363 of follower 360

With continued reference to FIGS. 2-4, instrument drive unit also includes a plurality of drive assemblies 300. In the illustrated embodiment, instrument drive unit 200 includes four drive assemblies 300, however instrument drive unit 200 may include more (e.g., five or six) or fewer (e.g., three) drive assemblies 300 without departing from the scope of the present disclosure.

With reference to FIGS. 5-9, each drive assembly 300 includes a proximal gear 310, a proximal bearing 320, a distal bearing 330, a drive screw 340, a drive nut 350, a follower 360, a biasing element 370, and drive member (e.g., a flexible cable) 380. Proximal gear 310 is configured to engage with an instrument control gear (e.g., crown gear "CG" of motor "M") of instrument control unit 100, such that rotation of crown gear "CG" causes a corresponding rotation of proximal gear 310. Proximal gear 310 may be a crown gear "CG" that is configured to mate with and/or mesh with crown gear "CG" of motor "M."

With particular reference to FIGS. 8 and 9, proximal gear 310 includes an aperture 312 extending longitudinally therethrough, which is configured to mechanically engage a proximal portion 342 of drive screw 340. As shown, aperture 312 and proximal portion 342 of drive screw 340 have corresponding, non-circular cross-sections, such that proximal gear 310 and drive screw 340 are keyed to one another, which results in a rotationally fixed connection therebetween. Accordingly, rotation of proximal gear 310 results in a corresponding rotation of drive screw 340.

Proximal bearing 320 is disposed about a proximal shaft 343 of drive screw 340 adjacent a portion of proximal housing 210, and distal bearing 330 is disposed about a distal shaft 344 of drive screw 340 adjacent a portion of distal housing 220 (see FIG. 10, for example). Each of proximal bearing 320 and distal bearing 330 permits or facilitates rotation of drive screw 340 with respect to housing assembly 205. Additionally, proximal bearing 320 may be configured to function as a proximal stop for follower 360, and distal bearing 330 may be configured to function as a distal stop for drive nut 350.

Drive screw 340 includes proximal portion 342, proximal shaft 343, distal shaft 344 and a threaded portion 345, and defines a longitudinal axis "A-A" extending through a radial center thereof (see FIG. 8). Rotation of proximal gear 310 causes drive screw 340 to rotate about longitudinal axis "A-A" in a corresponding direction and rate of rotation.

Drive nut 350 includes a threaded aperture 352 extending longitudinally therethrough, which is configured to mechanically engage threaded portion 345 of drive screw 340. Drive nut 350 is configured to be positioned on drive screw 340 in a manner such that rotation of drive screw 340 causes longitudinal movement of drive nut 350. That is, drive nut 350 and drive screw 340 are threadedly engaged with each other. Moreover, rotation of proximal gear 310 in a first direction (e.g., clockwise) causes drive nut 350 to move in a first longitudinal direction (e.g., proximally) with respect to proximal portion 342 of drive screw 340, and rotation of proximal gear in a second direction (e.g., counter-clockwise) causes drive nut 350 to move in a second longitudinal direction (e.g., distally) with respect to proximal portion 342 of drive screw 340. Drive nut 350 also includes a retention pocket 354 disposed proximally adjacent threaded aperture 352. Retention pocket 354 includes a larger inner diameter than threaded aperture 352, and is configured to house at least a portion of biasing element 370, as discussed in further detail below.

Drive nut 350 includes rail 353 extending longitudinally along an outer surface thereof, and which is configured to be slidably disposed in a longitudinally extending channel 206 formed in bore 207 of housing assembly 205 (see FIGS. 5-7 and 12, for example). Rail 353 of drive nut 350 cooperates with channel 206 of bore 207 of housing assembly 205 to inhibit or prevent drive nut 350 from rotating about longitudinal axis "A-A" as drive screw 340 is rotated.

Follower 360 includes rail 363 extending longitudinally along an outer surface thereof, and which is configured to be slidably disposed in longitudinal extending channel 206 formed in bore 207 of housing assembly 205 (see FIGS. 3, 5-7 and 12, for example). Rail 363 of follower 360 cooperates with channel 206 of bore 207 of housing assembly 205 to inhibit or prevent follower 360 from rotating about longitudinal axis "A-A" as drive screw 340 is rotated.

Follower 360 includes a non-threaded aperture 362 extending longitudinally therethrough, which is configured to slidingly engage threaded portion 345 of drive screw 340. That is, follower 360 is non-threadedly engaged with and slidably supported on drive screw 340. It is also disclosed that follower 360 does not engage drive screw 340, and that follower 360 is solely guided by the geometry (e.g., e.g., channel 206) of housing assembly 205. Follower 360 includes a retention pocket 364 disposed distally adjacent aperture 362. Retention pocket 364 includes a larger inner diameter than aperture 362, and is configured to house at least a portion of biasing element 370, as discussed in further detail below. Follower 360 also includes an engagement portion 366 disposed adjacent a radially outward surface thereof, which is configured to mechanically engage a proximal portion 382 of drive member 380.

In the illustrated embodiment, follower 360 is disposed proximally of drive nut 350, but the present disclosure also includes embodiments where follower 360 is disposed distally of drive nut 350. In such embodiments, retention pocket 354 of drive nut 350 would be disposed at a distal location thereof, and retention pocket 364 of follower 360 would be disposed at a proximal location thereof. Here, it is envisioned that follower 360 pushes drive member 380 distally, rather than follower 360 pulling drive member 380 proximally.

Biasing element 370, e.g., a compression spring, is configured to radially surround a portion of threaded portion 345 of drive screw 340. That is, drive screw 340 extends through an aperture 371 defined by and extending longitudinally through biasing element 370. Additionally, as seen in FIG. 9, a proximal portion 372 of biasing element 370 is configured for reception at least partially within retention pocket 364 of follower 360, and a distal portion 374 of biasing element 370 is configured for reception at least partially within retention pocket 354 of drive nut 350. In disclosed embodiments, proximal portion 372 of biasing element 370 is immovably fixed to follower 360, and distal portion 374 of biasing element 370 is immovably fixed to drive nut 350. It is envisioned that a compressed length of biasing element 370 is equal to or slightly smaller than a combined longitudinal length of retention pocket 364 of follower 360 and retention pocket 354 of drive nut 350, thus allowing contact between a proximal face 351 of drive nut 350 and a distal face 361 of follower 360 (see FIG. 6). While the illustrated embodiments show a particular type of biasing element 370 (i.e., a compression spring), other types of biasing elements are contemplated by the present disclosure.

Drive member 380 extends distally from follower 360, through a central bore 208 (FIGS. 2 and 10) of housing assembly 205, and is configured to mechanically engage a portion of surgical instrument 10, e.g., end effector 20. More particularly, each drive assembly 300 is oriented within housing assembly 205 such that the drive member 380 of each drive assembly 300 is centrally located within housing assembly 205 (see FIGS. 10-13), and extends through an elongated portion of surgical instrument 10 and into engagement with end effector 20, for example. It is envisioned that the surgical instrument 10 includes projections or the like to help guide or route drive members 380 between the drive assembly 300 and the end effector, for example.

Longitudinal translation of drive member 380 is configured to drive a function of end effector 20. For example, distal translation of a particular drive member 380 may be configured to approximate jaw members 22 and/or 24 with respect to the other, and proximal translation of drive member 380 may be configured to move at least one jaw member 22 away from the other jaw member 24, for instance. Additionally, distal translation of a drive member 380 of a different drive assembly 300 of instrument drive unit 200 may be configured to articulate jaw members 22, 24 in a first direction, and proximal translation of the this drive member 380 may be configured to articulate jaw members 22, 24 in a second direction.

Additionally, since drive member 380 may be flexible and follow a particular path through surgical instrument 10, including a central portion of housing assembly 205, it may be beneficial to maintain drive member 380 in tension to prevent slack or to reduce the amount of slack in drive member 380. Without the benefit of the present disclosure, a user who manually (e.g., by hand) opens or otherwise manipulates jaw members to inspect and/or clean the jaw members, for example, may exert a proximal force on at least one drive member. That is, opening jaw members of a surgical instrument may cause at least a portion of at least one of its drive members to move proximally. In systems where drive members are directly connected to a drive nut, and where the drive nut is threadedly engaged with a drive screw, the engagement between the drive screw and the drive nut would prevent proximal translation of the drive nut in response to proximal translation of the drive member. Accordingly, proximal movement of the drive member (e.g., caused by manipulating the jaw members) may cause the drive member to go slack, and may cause the drive member to fall off of pulleys within the surgical instrument and/or become dislodged from retention pockets, for example. Instrument drive unit 200 of the present disclosure prevents or minimizes the possibility of drive members 380 losing their tension and going slack.

Figure 6:
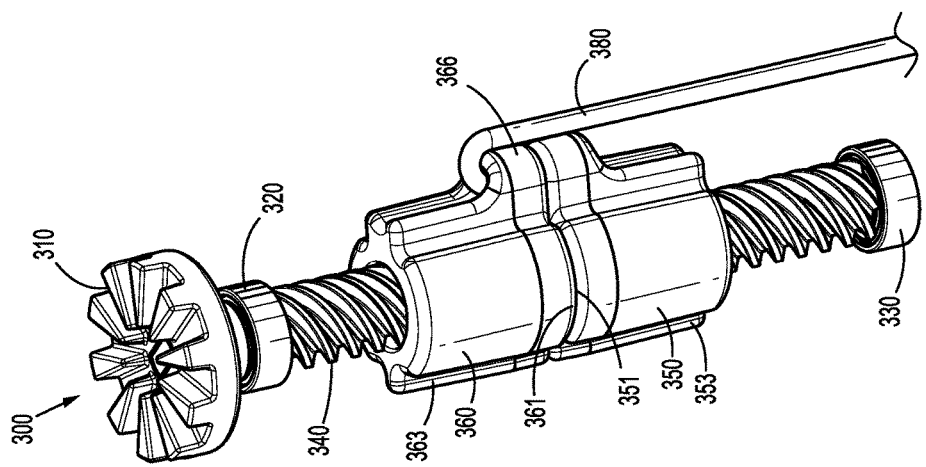

During a use of instrument drive unit 200 in the active state (i.e., when motor(s) "M" of instrument control unit 100 are used to rotate proximal gear(s) 310), rotation of proximal gear 310 results in a corresponding rotation of drive screw 340. Rotation of drive screw 340 causes longitudinal translation of drive nut 350 due to the engagement between threaded portion 345 of drive screw 340 and threaded aperture 352 of drive nut 350. As discussed above, the direction of longitudinal translation of drive nut 350 is determined by the direction of rotation of proximal gear 310, and thus drive screw 340. With particular reference to FIG. 6, which illustrates proximal face 351 of drive nut 350 abutted against distal face 361 of follower 360 (i.e., in the active state), proximal translation of drive screw 340 results in a corresponding proximal translation of follower 360, and thus a corresponding proximal translation of a respective drive member 380 which is engaged with follower 360.

Additionally, when one drive nut 350 moves in a first longitudinal direction (e.g., proximally), it is envisioned that a drive nut 350 from a different drive assembly 300 is forced to correspondingly move in a second, opposite longitudinal direction (e.g., distally). Such configurations function to compensate for any slack in drive members 380. Moreover, once all drive nuts 350 are engaged with respective followers 360 (e.g., compressing biasing element 370; see FIG. 6), and when the system is so-called "stiff" (i.e., no stretch in drive members 380), the sum of the displacements of the four drive members 380 must be zero. For example, if one drive member 380 moves distally two units, two other drive members 380 can move proximally one unit each, and the fourth drive member 380 would not move, thus preserving the net zero displacement.

This movement of drive nuts 350, followers 360 and drive members 380 is controlled by motors "M" and system controls. When a drive nut 350 moves distally without corresponding proximal movement of a drive member 380, the drive nut 350 would separate from follower 360 with that drive assembly 300 (see FIGS. 5 and 7). These features help achieve zero displacement by preventing slack in drive members 380.

Figure 7:
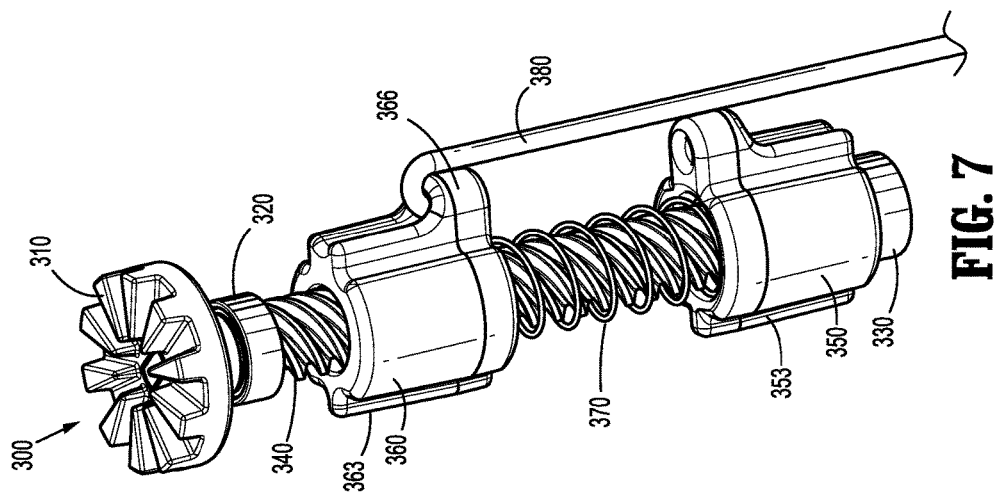
FIGS. 5-7 are perspective views of a drive assembly of the instrument drive unit of FIGS. 1C-4 shown at various points of operation.
Figure 5:
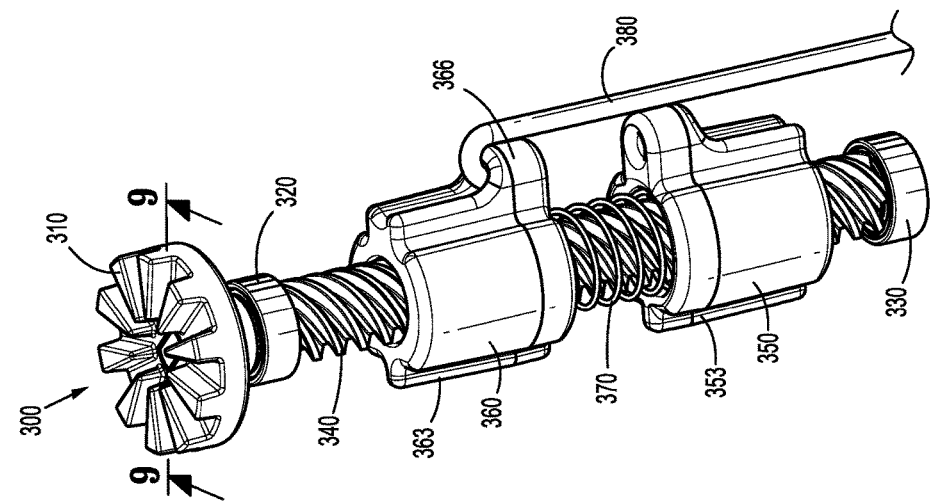

More particularly, in FIGS. 5 and 7, drive nut 350 has separated from follower 360. Here, this drive assembly 300 may not be capable of effectively translating a meaningful load to drive member 380, but drive member 380 and follower 360 are capable of translating relatively freely (or unimpeded) proximally and distally. Such a configuration or ability is helpful to allow a wrist assembly to be externally manipulated separate from the system control. In FIG. 5, drive nut 350 has been driven proximally such that biasing element 370 has been partially compressed; in FIG. 7 biasing element 370 has been compressed less than in FIG. 5 (e.g., biasing element 370 has not been compressed).

In FIG. 6, drive assembly 300 is in an "active use state" where drive nut 350 has been driven into contact with follower 360, and pre-tension has been added to drive member 380, for example. When each of the four drive assemblies 300 is in this position, the system is not back-drivable; an external force on the jaw members 22, 24 or wrist assembly would not result in movement of drive assemblies 300.

During use of instrument drive unit 200 in the passive state (i.e., when jaw members 22, 24 are being manipulated manually), manual manipulation of jaw members 22, 24 results in longitudinal movement of follower 360 while maintaining some level of tension of drive member 380. More particularly, in disclosed embodiments, manipulation of jaw members 22, 24 (e.g., moving one jaw member 22 away from the other 24) causes proximal movement of one drive member 380. As described above, proximal movement of a drive member in a different instrument (not employing the principles of the present disclosure) may cause the drive member to lose its tension or stretch and thus cause undesirable effects. Here, however, proximal movement of the one drive member 380 results in a corresponding proximal movement of follower 360 because follower 360 is slidable with respect to drive screw 340 and is not threadedly engaged therewith. At least some level tension in drive member 380 remains because biasing element 370, which is engaged with both follower 360 and drive nut 350, provides an opposite force against follower 360. That is, if the one drive member 380 is moved proximally, and thus exerts a proximal force on follower 360, this force is resisted and/or counterbalanced by biasing element 370, thus retaining tension in drive member 380. Likewise, if the one drive member 380 is moved distally and thus exerts a distal force on follower 360, this force is also resisted and/or counterbalanced by biasing element 370, thus retaining at least some level of tension in drive member 380.

The present disclosure includes a robotic surgical system including an instrument drive unit 200, an instrument control unit 100 including four independently-controlled motors "M," and a surgical instrument 10 including four drive assemblies 300, with each drive assembly 300 selectively connectable to a respective motor "M" of instrument control unit 100, for example, as described above. Additionally, the present disclosure includes methods of controlling a surgical instrument 10 including the use of instrument control unit 100 and instrument drive unit 200, and methods of performing a surgical task using instrument control unit 100 and instrument drive unit 200. The present disclosure further includes methods of manually manipulating jaw members 22, 24 while maintaining tension in drive members 380.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A drive assembly of an instrument drive unit for use with a surgical instrument, the drive assembly comprising:
    a drive screw defining a longitudinal axis, the drive screw including a threaded portion;
    a drive nut threadedly engaged with the threaded portion of the drive screw such that rotation of the drive screw results in longitudinal movement of the drive nut;
    a follower being longitudinally slidable with respect to the drive screw;
    a biasing element disposed in mechanical cooperation with the drive nut and the follower; and
    a drive element disposed in mechanical cooperation with the follower, wherein longitudinal translation of the drive element is configured to drive a function of the surgical instrument.

2. The drive assembly according to claim 1, wherein the follower is disposed proximally of the drive nut, and where the follower is biased proximally.

3. The drive assembly according to claim 1, wherein the drive element is secured to the follower, and wherein the drive element is longitudinally translatable with respect to the drive nut.

4. The drive assembly according to claim 1, wherein each of the drive nut and the follower includes a retention pocket configured to house a portion of the biasing element.

5. The drive assembly according to claim 1, wherein the biasing element is a compression spring.

6. The drive assembly according to claim 1, wherein the follower is disposed proximally of the drive nut, and wherein the drive element extends distally from the follower.

7. The drive assembly according to claim 1, wherein the follower is non-threadedly engaged with the drive screw.

8. The drive assembly according to claim 1, wherein the drive member includes a flexible cable.

9. The drive assembly according to claim 1, wherein the drive nut defines an aperture, wherein the follower defines an aperture, wherein the drive screw extends through the aperture of the drive nut and the follower.

10. The drive assembly according to claim 9, wherein the biasing element is disposed about the drive screw.

11. An instrument drive unit for use with a surgical instrument, the instrument drive unit comprising:
    a plurality of drive assemblies, each drive assembly comprising:
        a drive screw defining a longitudinal axis, the drive screw including a threaded portion;
        a drive nut threadedly engaged with the threaded portion of the drive screw such that rotation of the drive screw results in longitudinal movement of the drive nut;
        a biasing element disposed in mechanical cooperation with the drive nut; and
        a flexible drive element disposed in mechanical cooperation with the biasing element, longitudinal translation of the flexible drive element is configured to drive a function of jaw members of the surgical instrument.

12. The instrument drive unit according to claim 11, wherein each drive assembly further comprises a follower disposed in mechanical cooperation with the biasing element, the follower being longitudinally slidable with respect to the drive screw.

13. The instrument drive unit according to claim 12, further comprising a housing, wherein each drive assembly of the plurality of drive assemblies is housed at least partially within the housing, and wherein the follower includes a rail that is configured to slidingly engage a channel of the housing.

14. The instrument drive unit according to claim 11, wherein the biasing element is configured to maintain the flexible drive element in a tensile state during application of a mechanical force to the jaw members of the surgical instrument.

15. The instrument drive unit according to claim 11, wherein the biasing element is a compression spring.

16. The instrument drive unit according to claim 11, wherein the drive nut defines an aperture, and wherein the drive screw extends through the aperture of the drive nut.

17. The instrument drive unit according to claim 16, wherein the biasing element is disposed about the drive screw.

18. The instrument drive unit according to claim 11, wherein the plurality of drive assemblies includes four drive assemblies.

19. The instrument drive unit according to claim 11, further comprising a housing, wherein each drive assembly of the plurality of drive assemblies is housed at least partially within the housing, and wherein the flexible drive element of each drive assembly extends through a central bore of the housing.

20. The instrument drive unit according to claim 11, further comprising a housing, wherein each drive assembly of the plurality of drive assemblies is housed at least partially within the housing, and wherein the drive nut includes a rail that is configured to slidingly engage a channel of the housing.

\* \* \* \* \*